(12) United States Patent  
Lopez Quintela et al.

(10) Patent No.: US 9,315,380 B2  
(45) Date of Patent: Apr. 19, 2016

(54) USE OF ATOMIC QUANTUM CLUSTER (AQC) AS ANTIMICROBIAL AGENTS AND BIOCIDES

(75) Inventors: Manuel Arturo Lopez Quintela, Santiago de Compostela (ES); José Rivas Rey, Santiago de Compostela (ES); María Carmen Blanco Varela, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 608 days.

(21) Appl. No.: 12/681,642

(22) PCT Filed: Oct. 1, 2008

(86) PCT No.: PCT/ES2008/070180  
§ 371 (c)(1),  
(2), (4) Date: Apr. 5, 2010

(87) PCT Pub. No.: WO2009/043958  
PCT Pub. Date: Apr. 9, 2009

(65) Prior Publication Data  
US 2010/0215766 A1    Aug. 26, 2010

(30) Foreign Application Priority Data  
Oct. 5, 2007   (ES) .................................. 200702615

(51) Int. Cl.  
*A61K 33/24*    (2006.01)  
*A61K 33/38*    (2006.01)  
(Continued)

(52) U.S. Cl.  
CPC . *B82Y 5/00* (2013.01); *A61K 33/24* (2013.01); *A61K 33/26* (2013.01); *A61K 33/34* (2013.01); *A61K 33/38* (2013.01); *A61K 45/06* (2013.01); *B22F 1/0096* (2013.01); *B82Y 30/00* (2013.01)

(58) Field of Classification Search  
CPC ....... A61K 33/24; A61K 33/38; A61K 45/06; B22F 1/00; B22F 9/00  
See application file for complete search history.

(56) References Cited

U.S. PATENT DOCUMENTS

2003/0108612 A1   6/2003 Xu  
2003/0180378 A1   9/2003 Gillis  
(Continued)

FOREIGN PATENT DOCUMENTS

| ES | 2277531 | 7/2007 |
| WO | WO 2006049477 A1 * | 5/2006 |
| WO | WO 2007017550 | 2/2007 |

OTHER PUBLICATIONS

Coloplast MSDS (www.us.coloplast.com, Dec. 2010).*

(Continued)

*Primary Examiner* — Ernst V Arnold  
*Assistant Examiner* — Kyung Sook Chang  
(74) *Attorney, Agent, or Firm* — Merchant & Gould P.C.

(57) ABSTRACT

The invention relates to the use of stable atomic quantum clusters (AQC) with antimicrobial activity. The stable AQCs include at least 500 metal atoms (Mn, n<500), the metals being selected from among Au, Ag, Co, Cu, Pt, Fe, Cr, Pd, Ni, Rh, Pb or bi- or multi-metallic combinations thereof. Said AQCs are used as antimicrobial agents, antifungal agents and biocides at concentrations of the order of between 1 nM and 100 nM or more in relation to atoms of the corresponding metal. The antimicrobial activity is specific to both the type of metal and size of cluster used.

14 Claims, 3 Drawing Sheets

(51) Int. Cl.
*A61K 45/06* (2006.01)
*B22F 1/00* (2006.01)
*B22F 9/00* (2006.01)
*B82Y 5/00* (2011.01)
*A61K 33/26* (2006.01)
*A61K 33/34* (2006.01)
*B82Y 30/00* (2011.01)

(56) References Cited

U.S. PATENT DOCUMENTS

2006/0204591 A1* 9/2006 Burrell et al. ................ 424/618
2006/0280785 A1 12/2006 Easterly
2009/0035852 A1 2/2009 Lopez Quintela

OTHER PUBLICATIONS

Hanikenne et al., "Transition Metal Nutrition: A Balance Between Deficiency and Toxicity", Chapter 10, pp. 333-399, (Sep. 26, 2008).*
International Search Report of PCT/ES2008/070180 (WO2009/043958) mailed Jan. 27, 2009.
Barnett, et al., Eur. Phys. J. D., 1999, 9:95-104.
Boyen, et al., Science, 2002, 297, 1533-1536.
Brust, et al., J. Chem. Soc. Chem. Commun., 1994, 801-802.
Cioffi, et al., Anal. Bioanal. Chem., 2005, 382:1912-1918.
Crespo, et al., Physical Review Letters, 2004, 93:8, 1-4.
Fojtik, et al., The Journal of Physical Chemistry, 1992, 96:21, 8203-8206.
Jimenez, et al., Anal. Chem., 2003, 75:199-206.
Kim, et al., Nanomedicine: Nanotechnology, Biology and Medicine, 2007, vol. 3, 95-101.
Lee, et al., J. Am. Chem. Soc., 2004, 126:19, 6193-6199.
Lee, et al., J. Mater. Sci., 2003, 38, 2199-2204.
Lee, et al., J. Phys. Chem. B., 2003, 107:9994-10005.
Lok, et al., J. Biol. Inorg. Chem., 2007, 12:4, 527-534.
Pal, et al., Appl. Environ. Microbiol., 2007, 73:6, 1712-1720.
Petty, et al., J. Am. Chem. Soc., 2004, 5207-5212.
Peyser, et al., Science, 2001, 291, 103-106.
Peyser-Capadona, et al., Physical Review Letters, 2005, 94, 058301, 1-4.
Rodriguez-Sanchez, et al., J. Phys. Chem. B., 2005, 109, 1183-1191.
Schaaff, et al., J. Phys. Chem. B., 2000, 104, 2630-2641.
Schmid, et al., Advanced Engineering Materials, 2001, 3:10, 737-743.
Sondi, et al., J. Colloid Interface Sci., 2004, 275, 177-182.
Spadaro, et al., Microb. Agents Chemother., 1974, 6:5, 637-642.
Zhang, et al., Chemical Physics., 2006, 330, 495-500.
Zheng, et al., Physical Review Letters, 2004, 93:7, 1-4.

* cited by examiner

USE OF ATOMIC QUANTUM CLUSTER (AQC) AS ANTIMICROBIAL AGENTS AND BIOCIDES

This application is a National Stage Application of PCT/ES2008/070180, filed 1 Oct. 2008, which claims benefit of Serial No. P200702615, filed 5 Oct. 2007 in Spain and which applications are incorporated herein by reference. To the extent appropriate, a claim of priority is made to each of the above disclosed applications.

The present invention proposal describes the use of the antimicrobial and biocidal activity exhibited by Atomic Quantum Clusters (AQCs) of various metals synthesised according to the process described in the patent of invention application P200502041 and the AQCs claimed in the corresponding international application WO 2007/017550.

STATE OF PRIOR ART

Although the use of metals such as gold and silver as bactericides and biocides has been known since ancient times, there is no unanimous agreement about their mode of action, which seems to depend on their form, size and method of preparation. Thus, for example, Pal et al. [S. Pal, Appl. Environ. Microbiol. 2007, 73, 1712] showed that the geometry of the nanoparticles plays a very important role in their activity against *Escherichia coli*. Similarly, Cioffi et al. [N. Cioffi, Anal. Bioanal. Chem., 2005, 382, 1912] showed antimicrobial activity against *Escherichia coli* and *Saccharomyces cerevisiae* of Ag and Cu nanoparticles of sizes between 1.7 nm and 6.3 nm, obtained electrochemically in the presence of tetraoctylammonium salts. Also, these authors showed that the introduction of the particles into an inert polymer did not reduce their antimicrobial activity. Lee et al. [H. J. Lee, J. Mater. Sci. 2003, 38, 2199] showed that 2-5 nm silver particles also exhibited antimicrobial activity against a Gram-positive bacterium, *Staphylococcus aureus*, as well as against a Gram-negative bacterium, *Klebsiela pneumoniae*, and that this activity was preserved when the nanoparticles were introduced into cotton or polyester fibres. Similarly, Sondi et al. [I. Sondi, J. Colloid Interface Sci. 2004, 275, 177] also observed bactericide activity against *E. coli* of 12 nm Ag nanoparticles covered in a high molecular weight surfactant. Also, Xu et al. in the patent US2003108612A1 described the use of metal nanoparticles as a method for the inhibition of bacterial growth and treatment of diseases caused by bacteria.

Although in this patent, the claims indicate that the particles exhibiting these properties must have sizes of 100 nm or less, the patent states several times that the ideal sizes must be between 50 to 100 nm. Therefore this patent of invention reveals that the size, provided it is between these intervals (less than 100 nm), does not appreciably affect the antibacterial properties. The particles described in this patent are also characterised, apart from their sizes obtained by electronic transmission microscopy and dark field microscopy, by the position of their plasmon band in visible spectroscopy.

From the above, despite many studies carried out to date, the mechanism by which nano/microparticles exhibit antibacterial/biocidal behaviour under certain conditions is still unknown. Due to the fact that direct use of metal salts (mainly gold, silver and copper) also shows antibacterial properties [see for example, J. A. Spadaro, et al., Microb. Agents Chemother. 6 (1974) 637] one of the current hypotheses is that the metal micro/nanoparticles can serve as a metal ion reservoir, releasing ions that act as bactericides/biocides. Thus, for example, C. E. Easterly et al. in the patent application US2006280785A1 used this idea by means of the incorporation of Ag nanoparticles of sizes<10 nm in liposomes of sizes<85 nm. The preferred use of nanoparticles in the size interval of 1 nm to 10 nm relies on the intent to dissolve the nanoparticles, generating a constant concentration of metal ions. The fact of using metal particles of the sizes described is due to the low stability exhibited by nanoparticles as their size decreases.

The Spanish patent application P200502041 and its international application WO 2007/017550 describe a process for obtaining atomic quantum clusters, denominated AQCs, and identify particles with sizes less than 1 nm-2 nm of various metals. Also described are how to separate, stabilise and use them; the details of the method indicate that the physico-chemical properties of the clusters synthesised by this process are different from nanoparticles (particles larger than 1 nm-2 nm). This is because there is a separation of energy Fermi levels ("HOMO-LUMO" gap or bandgap) in AQCs that causes these particles to stop behaving like metals; this is easily observed in the suppression of their plasmon band, and the appearance of different bands due to electron transitions between the different energy levels of the clusters. They stop behaving in a "metallic" way and their behaviour becomes molecular in nature. Thus new properties appear in these clusters that are not observed in nanoparticles, microparticles or bulk metal materials. Because the physico-chemical properties of AQCs cannot be simply extrapolated from that of nano/microparticles, then the properties shown by these clusters cannot in principle be predicted from the properties shown by nano/microparticles, such as the antibacterial properties described above for nanoparticles and metal ions. The AQCs (in contrast to nanoparticles that require "stabilisation" for charge or steric hindrance by some protective molecule) exhibit extraordinary stability precisely because of the existence of this Fermi level "gap". That is, clusters, as opposed to nanoparticles, do not dissolve to generate ions so that in principle, the extrapolation that they have bactericide properties, as described in the patent application US2006280785 A1, also cannot be made.

DESCRIPTION OF THE INVENTION

The present invention refers to the use of stable atomic quantum clusters, AQCs, that is, groups of atoms with the number of atoms being less than 500 (corresponding to a size of approximately 2 nm), as antimicrobial, antifungal and biocidal agents. AQCs are understood to be:

AQCs, stable atomic quantum clusters,

AQCs characterised by being composed of less than 500 metal atoms ($M_n$, $n<500$), AQCs characterised by being composed of less than 200 metal atoms ($M_n$, $n<200$), AQCs characterised by being composed of between more than 2 and less than 27 metal atoms ($M_n$, $2<n<27$), AQCs characterised by being composed of between 2 and 5 metal atoms, AQCs where the metals are selected from Au, Ag, Co, Cu, Pt, Fe, Cr, Pd, Ni, Rh, Pb or bi- and multi-metal combinations, AQCs where the metal is Au or Ag or their combinations.

Biocides are understood to be active and prepared substances, containing one or more active substances, presented in the form in which they are administered to the user, intended to destroy, counteract, neutralise, impede the action or execute control of some other type over any harmful organism by chemical or biological means.

It will also be shown that the mechanism of action of these AQCs is different from that of micro/nanoparticles as the clusters exhibit antimicrobial activities, while 5 nm nanoparticles tested as controls at concentrations (expressed in numbers of corresponding metal atoms) of even 100,000 times higher than that of the AQCs do not exhibit any activity, as will be described in the examples below. In addition, in contrast to what is observed with nanoparticles (referring to for example the patent US2006280785A1), the clusters exhibit certain specificity against various pathogens, both by the size of the cluster and by the type of metal element used, as will be shown in the examples described below. Lastly, the mechanisms are also different from those that might occur with metal salts for the same purpose, as metal salts have been used as controls and no antibacterial activity was observed under the same experimental conditions, even at concentrations 100,000 times higher than those of the clusters.

The AQCs of the present invention exhibit antimicrobial and biocidal activities at concentration of the order of 1 nM (expressed in atoms of the corresponding metal) that is of the order of 100,000 times less than the minimum inhibition concentration (MIC) normally used in studies of the antimicrobial activity of nanoparticles (see for example that cited in patent US2003108612A1), which demonstrates that the mechanism of action is also different. Furthermore, due to the extreme stability, these clusters can be used directly without the need to use any vehicle, avoiding processes such as that described in patent application US2006280785A1 for the use of nanoparticles as bactericidal agents.

The present invention is based on the surprising fact that the AQCs exhibit antimicrobial, antifungal and biocidal properties.

The bacteria against which the AQCs act include:

Gram-positive bacteria selected among the group *Staphylococcus aureus, Staphylococsus epidermidis, Streptococcus pneumoniae, Streptococcus agalactiae, Enterococcus faecalis* and *faecimus, Corynebacterium diphtheriae, Listeria monocytogenes, Bacillus anthracis, Clostridium perfringens, Clostridium difficile, Clostridium botulinum, Clostridium tetanus*, and *Clostridium novyi*.

Gram-negative bacteria selected among the group *Pseudomonas aeruginosa, Neisseria gonorrheae, Neisseria meningitidis, Haemophilus influenzae, Haemophilus parainfluenza, Haemophilus haemolyticus, Haemophilus parahaemolyticus, Haemophilus aphrophilus, Klebsiella pneumoniae, Campylobacter foetus, Campylobacter jejuni, Campylobacter coli, Helicobacter pylori, Vibrio cholerae, Vibrio opticus, Salmonella typhimurium, Salmonella* spp, *Shigella sonnei, Shigella boydii, Shigella flexneri, Shigella dysenteriae, Escherichia coli, Brucella melitensis, Brucella abortus, Brúcela suis, Rickettsia rickettsii, Francisella tularensis, Pasteurella multocida, Yersinia pestis, Acinetobacter baumani, Yersinia enterocolitica, Yersinia pseudotuberculosis, Proteus mirabilis, Bacteroides* species, *Fusobacterium* species, *Bordetella pertussis* and *Legionella pneumophilia*.

anaerobic, acid-alcohol resistant, spiral, *rickettsia, mycoplasma, actinomyces* bacteria and miscellaneous bacteria which for example include *Chlamidea, Chlamydophila, Mycoplasma Pneumonie, Rickettsia, Mycobacterium, Treponema pallidum, Treponema pertenue, Treponema carateum, Leptospira interrogans, Borrelia hermsii, Borrelia turicatae, Borrelia parkeri* and *Borrelia burgdorferi, Mycobacterium tuberculosis, Mycobacterium Bovis, Mycobacterium africanum, Mycobacterium microtii* and *Mycobacterium leprae*.

The fungi against which the AQCs act include *Actinomices, Aspergilus, Blatomyces, Cándida, Cromoblastomices, Cocidios, Criptococcus, Dermatophitos, Fusarius, Histoplasma, Madura, Mocor, Nocardia, Paracocidius, Penicillinum, Phaeohyphomyces, Scedosporium* and *Sporotricum*.

They can also be used in combination with other antifungal agents such as, for example, Amphotericin, Caspofungin, Micafungin, Anidulafungin, Fluconazole, Flucytosine, Griseofulvin, Imidazole, Itraconazole, Ketoconazole, Miconazole, Nystatin, Posaconazole, Terbinafine and Voriconazole.

The present invention can be used for the treatment of a disease caused by bacteria or for the inhibition of bacterial growth. Its use in nosocomial infections by agents that have become resistant to traditional antibiotics is especially indicated.

The object of the invention can also be used in vitro for all those cases where bacterial growth is undesirable or for the preparation of clinical diagnostic test kits.

The object of the invention can be used to confer antibacterial properties to other materials such as polymers and plastics; as well as to surgical and hospital materials such as bandages, dressings, and disinfecting dispersions and solutions.

AQCs are suitable for the preparation of a medicine or a phytosanitary product for the treatment of pathological or physiological states in people, animals and plants.

AQCs are suitable for the preparation of a medicine to be administered by transdermal, transmucosal, buccal, oral, rectal, ocular, nasal, optic, topical, vaginal or parenteral routes.

AQCs are suitable for the preparation of cosmetics and disinfectants.

AQCs are particularly indicated when the bacterium is resistant to an antibiotic other than the AQCs. The administration of AQCs can be combined with that of other types of antibiotics, including as examples, penicillins and related medicines, carbapenems, monobactams, fluoroquinolones, parenteral and oral cephalosporins, aminoglycosides, macrolides, ketolides, tetracyclines, glycylcyclines, glycopeptides, nitrofurantoins, Fosfomycin, Rifamycin, Metronidazole, Quinupristin, Linezolid, Daptomycin, Chloramphenicol, Clindamycin, fusidic acid, Trimethoprim and Celestine.

AQCs can also be used in combination with nanoparticles that exhibit known antibiotic activity.

AQCs are indicated for conferring biocidal properties to various formulations such as paints, sealants, polymers and plastics.

AQCs can also be used in construction materials, automation and textiles.

AQCs can be used alone or in combination with other known biocides.

AQCs are especially suitable as biocides for water treatment.

For the use of AQCs, both in antibacterial and biocide applications, the concentration to use (referring to atoms of the corresponding metal) is approximately 1 nM to 100 nM or higher.

Throughout the description and the claims, the word "comprise" and its variants is not intended to exclude other technical characteristics, additives, components or steps. For experts in the field, other objects, advantages and characteristics of the invention will become apparent partly from the description and partly from the practice of the invention. The following examples and figures are provided by way of illustration and are not intended to be limiting of the present invention.

DETAILED DESCRIPTION OF METHODS OF EMBODIMENT

Figure 1:
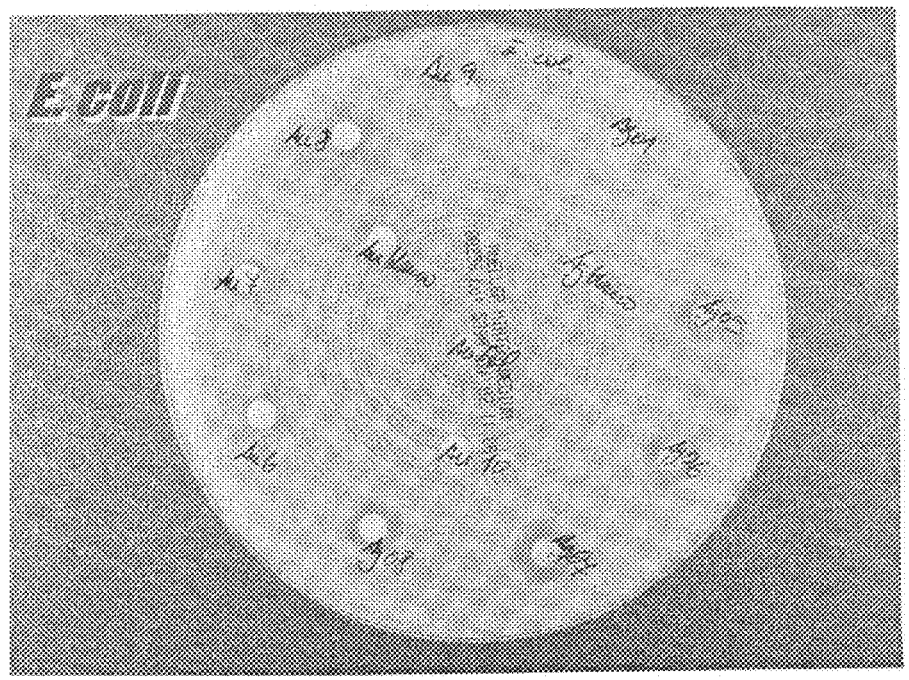
FIG. 1.—Shows the halos obtained for growth inhibition experiments against *E. coli* ATCC 90028.

The following examples clearly show the antimicrobial and biocidal properties of AQCs. Example 1 describes the preparation of AQC samples whose antibacterial properties are described in Example 2. Example 1 also describes the nanoparticles and corresponding metal salt controls used to compare their antimicrobial activity, which are also reflected in Example 2. Example 3 describes the preparation of the AQC samples used in biocidal activity trials as well as that of the controls and reference biocidal samples.

EXAMPLE 1

Preparation of the AQCs, nanoparticles samples and control samples.

Ag01; Ag05; Ag06; Ag07; Ag08. Ag control.

Au6; Au7; Au8; Au9. Au control (samples Au6-8). Au10. Au control (sample Au10).

1) Ag control sample: 100 µM $AgNO_3$ and 200 µM tetrabutylammonium bromide solution.

Samples Ag05-Ag08: AQCs of Ag.

The synthesis of AQCs of Ag was carried out in an electrochemical cell using galvanostatic potentiometry, applying a constant current density of 0.2 $mA/cm^2$ for different times (t) under the following experimental conditions: Working electrode: Pt (6 $cm^2$). Contraelectrode: Ag. Reference electrode: Ag/AgCl. Electrolyte solution: 200 µM tetrabutylammonium bromide in water.

Temperature: 25° C.

The final samples were diluted in water to obtain a final concentration of 100 nM clusters in atoms of Ag.

All the samples exhibited two UV absorption peaks at 211 nm and 227 nm as well as a small narrow band centred around 260 nm.

The synthesis times used were:

2) Sample Ag05; t=210 minutes.
3) Sample Ag06; t=90 minutes.
4) Sample Ag07; t=65 minutes.
5) Sample Ag08; t=55 minutes.
6) Sample Ag01: Nanoparticles of Ag.

The synthesis of silver nanoparticles was performed by reaction between PVP, poly(N-vinyl-2-pyrrolidone), of molecular weight PM=10,000 and silver nitrate. Firstly, a 50 ml solution of 20 nM $AgNO_3$ was prepared. Then 20 g of PVP was weighed into a 250 ml precipitation flask and dissolved in distilled water. Water was added to reach a total of 91.25 ml. To this solution, 8.75 ml of silver nitrate solution were added. The flask was placed in a water bath at 70° C. for 4 hours. Once the reaction was complete, an excess of acetone was added to precipitate the nanoparticles. Part of the solvent was removed by decantation and the remainder was removed by evaporation in an oven. The sample obtained, dispersed in water, exhibited an absorption band at 410 nm, characteristic of the plasmon band of Ag particles. The size of the nanoparticles, measured by TEM, was 6 nm. The sample for microbiological assays was prepared by performing a washing stage with 10 ml acetone to a solution of 0.5 g in 10 ml water, in order to remove excess PVP. The resulting solution was finally diluted to obtain a solution of 100 nM of Ag nanoparticles.

7) Au control sample: 100 µM $HAuCl_4$ and 200 µM TBABr (tetrabutylammonium bromide) in a 1:1 mixture of acetonitrile/water.

Samples Au6-Au9: AQCs of Au.

The synthesis of AQCs of Au was carried out in an electrochemical cell using galvanostatic potentiometry, applying a constant current density of 10 $mA/cm^2$ for different times under the following experimental conditions: Working electrode: Pt (2.5 $cm^2$). Contraelectrode: Au. Reference electrode: Ag/Ag Cl.

Electrolyte solution: 0.1 M tetrabutylammonium bromide in a 1:1 mixture of acetonitrile/water.

Inert atmosphere of nitrogen.

Temperature: 25° C.

The final samples were diluted in a 1:1 mixture of acetonitrile/water to obtain a final concentration of clusters of 100 nM in atoms of Au.

All the samples exhibited two UV-visible absorption peaks at 260 nm and 390 nm in addition to a small peak at 470 nm. Samples Au6 and Au7 also exhibited an additional peak at 300 nm.

The synthesis times used were:

8) Sample Au6; t=200 s.
9) Sample Au7; t=150 s.
10) Sample Au8; t=100 s.
11) Sample Au9; t=50 s.
12) Sample AuW: Nanoparticles of Au.

The synthesis of gold nanoparticles was carried out by the method of Brust [M. Brust, et al. J. Chem. Soc. Chem. Commun. 1994, 801]. For this, two solutions were prepared. Firstly, 10 ml of 30 mM $HAuCl_4$. Secondly, 0.670 g of TOABr (tetraoctylammonium bromide) were dissolved in 24 ml toluene. The Au(III) solution was introduced into a 100 ml flask with a stirring bar and the TOABr solution was added slowly with stirring, producing an exchange of the Au(III) salt with the organic phase. Then, 0.114 g $NaBH_4$ were dissolved in 30 ml $H_2O$ (0.1 M) and added slowly using a funnel, drop by drop, over the earlier mixture. The hydride reduces the Au salt and the sample takes on an intense red colour characteristic of Au nanoparticles. Finally, the sample was purified. To do this, the aqueous phase was separated. The organic phase was washed with 25 ml of 0.1 M $H_2SO_4$. It was then washed 5 times with 25 ml distilled water and finally dried with anhydrous $Na_2SO_4$. The sample obtained, dispersed in toluene, exhibited an absorption band at 540 nm, characteristic of the plasmon band of Au nanoparticles. The size of the nanoparticles, measured by TEM, was 5 nm. The final sample used in microbiological assays was obtained by dissolving 333 µl of the above product in the corresponding quantity of toluene so that the final particle concentration was 100 µM.

13) Sample Tol Control

Sample containing 100 µM $HAuCl_4$ and 200 µM TOABr in toluene. Dried with anhydrous $Na_2SO_4$, filtered through a folded filter and finally through a 0.2 micron filter.

EXAMPLE 2

Antimicrobial activity assays. All the samples were sterilised by filtration through 0.22 micron membranes. The method used for antimicrobial activity assays was that of disc-diffusion. The cellulose discs were loaded for the assays by immersion in AQC solutions and then dried at 4° C. The amount of cluster solution adsorbed by the discs of the present example was 25±1 ml. The growth medium used was Agar Mueller-Hilton. The microbial suspension used was 0.5 McFarland. The microorganisms trialled were:
E. coli ATCC 25922
E. faecalis ATCC 29212
P. aeruginosa ATCC 27853
S. aureus ATCC 29213
C. albicans species obtained from a clinical sample The microorganisms were incubated for 24 hours at 35° C. in an aerobic atmosphere.

Figure 2:
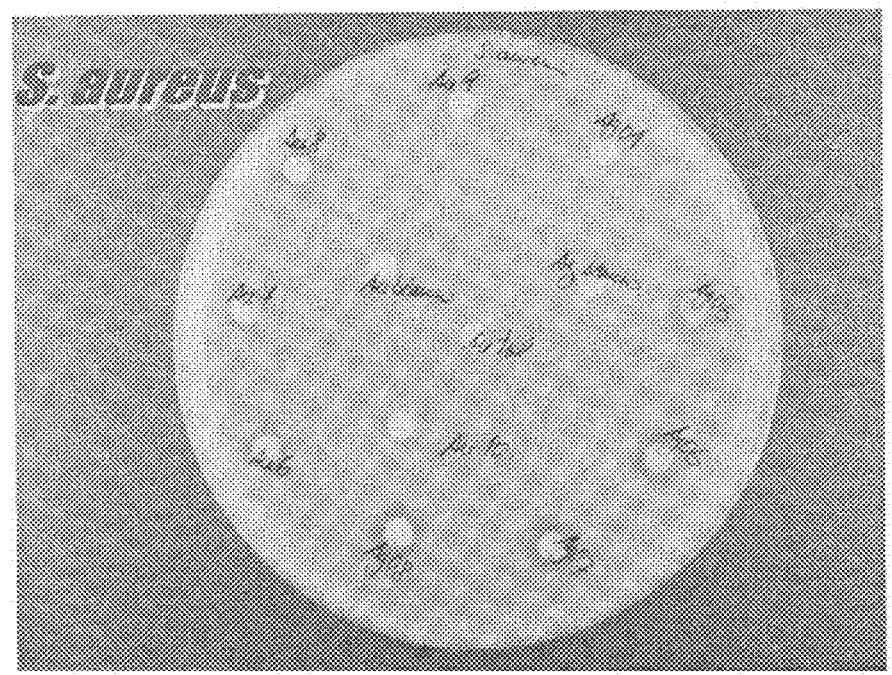
FIG. 2.—Shows the halos obtained for growth inhibition experiments against *Staphylococcus aureus* ATCC 29213.
Figure 3:
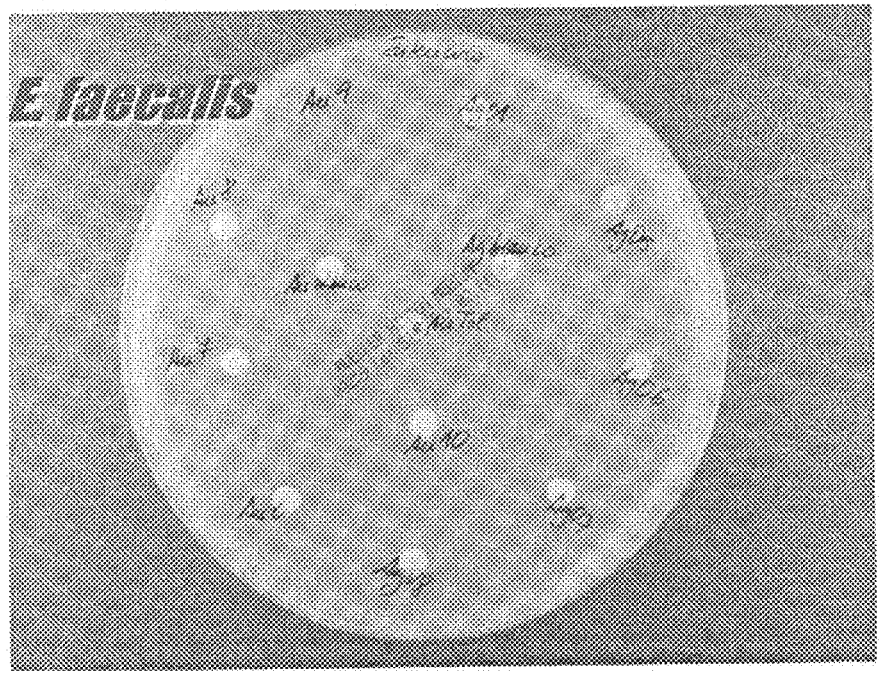
FIG. 3.—Shows the halos obtained for growth inhibition experiments against *Enterococcus faecalis* ATCC 29212.
Figure 4:
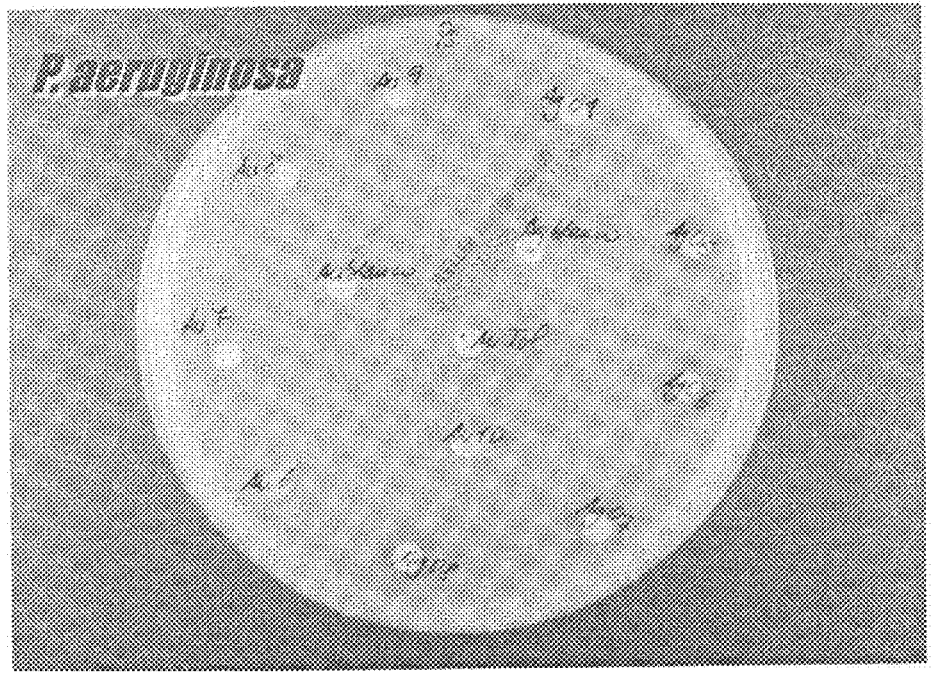
FIG. 4.—Shows the halos obtained for growth inhibition experiments against *Pseudomonas aeruginosa* ATCC 27853.
Figure 5:
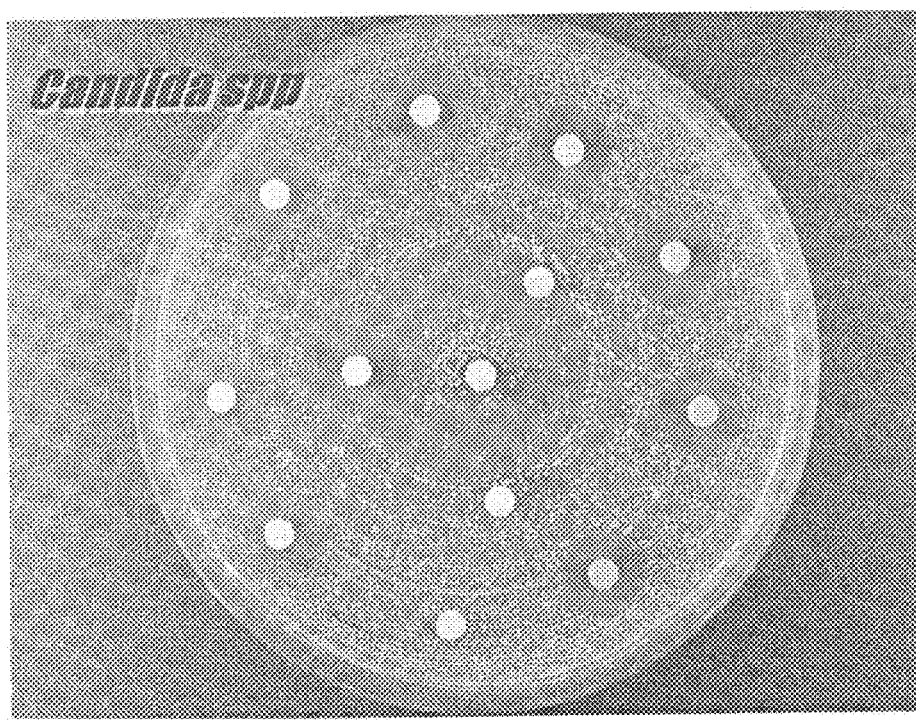
FIG. 5.—Shows the halos obtained for growth inhibition experiments against *Candida* species.

FIGS. 1 to 5 show the halos observed with the various AQCs tested, as well as with the nanoparticles and corresponding salts tested as controls. Table 1 shows the halo diameters observed using a 6 mm diameter cellulose disc.

Table 1.—Results of the inhibition halos observed (expressed in mm) against various microorganisms for the experiments described in Example 2.

|  | Ag Blank | Ag 01 | Ag 05 | Ag 06 | Ag 07 | Ag 08 |
|---|---|---|---|---|---|---|
| C. albicans ATCC 90028 | 6 | 6 | 15 | 16 | 17 | 17 |
| E. coli ATCC 25922 | 6 | 6 | 10 | 10 | 12 | 10 |
| E. faecalis ATCC 29212 | 6 | 6 | 6 | 6 | 6 | 6 |
| P. aeruginosa ATCC 27853 | 6 | 6 | 11 | 11 | 10 | 10 |
| S. aureus ATCC 29213 | 6 | 6 | 11 | 11 | 11 | 11 |

|  | Au Blank | Au 06 | Au 07 | Au 08 | Au 09 | Tol Blank | Au 10 |
|---|---|---|---|---|---|---|---|
| C. albicans ATCC 90028 | 6 | 8 | 6 | 6 | 6 | 6 | 6 |
| E. coli ATCC 25922 | 6 | 9 | 8 | 9 | 6 | 6 | 6 |
| E. faecalis ATCC 29212 | 6 | 6 | 6 | 6 | 6 | 6 | 6 |
| P. aeruginosa ATCC 27853 | 6 | 6 | 6 | 6 | 6 | 6 | 6 |
| S. aureus ATCC 29213 | 6 | 9 | 6 | 6 | 6 | 6 | 6 |

From the antimicrobial trials, the following are deduced:
a) Ag Samples

For Ag samples, it can be seen that the Ag control (Ag+ ions) and the Ag01 sample (Ag nanoparticles) did not give inhibition halos in any of the assays. The Ag AQCs have halos in all assays, except in the case of E. faecalis. It can also be seen that the halos for C. albicans are bigger for all AQC samples assayed.
b) Au Samples For Au samples, it can be observed that $Au^{3+}$ ions [either in acetonitrile-water mixture (Au control) or in toluene (Tol control)] and Au nanoparticles (Au10) did not give any inhibition halos. The AQC samples exhibited different behaviours depending on the sample type. Thus, sample Au6 exhibited inhibition halos only against C. albicans, E. coli and S. aureus. Samples Au7 and Au8 exhibited activity only against E. coli. Lastly, sample Au9 did not exhibit any activity.

Thus, it has been demonstrated that the AQC activity is different depending on the type of material (Au or Ag in these specific examples) and also depending on the size within the same material (which is related to the synthesis time according to that indicated in patent application No. P200502041 and its extension PCT/ES2006/070121. The higher activity of the AQCs than the salts and nanoparticles of the metals trialled has also been clearly shown as the latter did not exhibit any activity under the conditions in which the assays were performed.

EXAMPLE 3

For the study of the biocidal activity of the AQCs, three different samples were prepared.

Sample B1: a water-based paint-coating was prepared with a styrene acrylic copolymer adjuvant in 50% aqueous dispersion and a pigment-volume concentration of 22%, pigmented with titanium oxide and with a viscosity of 3 Pa·s. This sample was used as a control. Sample B2: To sample B1, a sample of 5 μM of Ag05 AQC was added (see Example 1), diluted in the final sample to 0.2%, which is equivalent to a final concentration of clusters in the paint of 10 nM.

Sample B3: To sample B1, a sample of 5 μM of Ag05 AQC was added (see Example 1), diluted in the final sample to 0.4%, which is equivalent to a final concentration of clusters in the paint of 20 nM.

The samples were stored in closed 100 ml containers and maintained at ambient temperature (22° C.) for 3 months. It was observed that in the samples containing AQCs (B2 and B3), a small anaerobic fermentation had started, which was manifested by a homogenous bubbling in the container. However, no changes in viscosity were seen in the samples compared to the initial viscosity (3 Pa·s). By contrast, the sample used as a control, apart from the anaerobic fermentation that was observed, exhibited a sharp fall in viscosity (1 Pa·s), indicating the clear degradation of the polymer under the test conditions. This example clearly shows the biocidal activity of AQCs for inhibiting the degradation of polymers used in paint-coating formulations.

The invention claimed is:

1. A method for the inhibition of the growth of a microorganism, comprising:
   contacting the microorganism with 1 to 100 nM of stable Atomic Quantum Clusters (AQCs), the AQCs consisting of between 2 to less than 27 Au atoms and clusters of 2 to less than 27 Ag atoms.

2. The method of claim 1, wherein the AQCs consist of 2 to 5 metal atoms.

3. The method of claim 1, wherein the microorganism is a bacteria or a fungus.

4. The method of claim 1, wherein the microorganism is a bacteria selected from among a Gram-positive bacteria, a Gram-negative bacteria, an anaerobic bacteria, an acid-alcohol resistant bacteria, a spiral bacteria, a *rickettsia* bacteria, a *mycoplasma* bacteria, and an *actinomyces* bacteria.

5. The method of claim 4, further comprising contacting the bacteria with an agent selected from among a penicillin, a carbapenem, a monobactam, a fluoroquinolone, a cephalosporins, an aminoglycoside, a macrolide, a ketolide, a tetracycline, a glycylcycline, a glycopeptide, a nitrofurantoin, Fosfomycin, Rifamycin, Metronidazole, Quinupristin, Linezolid, Daptomycin, Chloramphenicol, Clindamycin, fusidic acid, Trimethoprim and Celestine.

6. The method of claim 1, wherein the microorganism is a Gram positive bacteria selected from among *Staphylococcus aureus, Staphylococsus epidermidis, Streptococcus pneumoniae, Streptococcus agalactiae, Enterococcus faecalis* or *faecimus, Corynebacterium diphtheriae, Listeria monocytogenes, Bacillus anthracis, Clostridium perfringens, Clostridium difficile, Clostridium botulinum, Clostridium tetanus,* and *Clostridium novyi*.

7. The method of claim 1, wherein the microorganism is a Gram negative bacteria selected from among *Pseudomonas*

*aeruginosa, Neisseria gonorrheae, Neisseria meningitidis, Haemophilus influenzae, Haemophilus parainfluenza, Haemophilus haemolyticus, Haemophilus parahaemolyticus, Haemophilus aphrophilus, Klebsiella pneumoniae, Campylobacter foetus, Campylobacter jejuni, Campylobacter coli, Helicobacter pylori, Vibrio cholerae, Vibrio opticus, Salmonella typhimurium, Salmonella* species, *Shigella sonnei, Shigella boydii, Shigella flexneri, Shigella dysenteriae, Escherichia coli, Brucella melitensis, Brucella abortus, Brúcela suis, Rickettsia rickettsii, Francisella tularensis, Pasteurella multocida, Yersinia pestis, Acinetobacter baumani, Yersinia enterocolitica, Yersinia pseudotuberculosis, Proteus mirabilis, Bacteroides* species, *Fusobacterium* species, *Bordetella pertussis*, and *Legionella pneumophilia.*

8. The method of claim 1, wherein the microorganism is a bacteria selected from among *Chlamydia, Chlamydophila, Mycoplasma Pneumonie, Rickettsia, Mycobacterium, Treponema pallidum, Treponema pertenue, Treponema carateum, Leptospira interrogans, Borrelia hermsii, Borrelia turicatae, Borrelia parkeri* and *Borrelia burgdorferi, Mycobacterium tuberculosis, Mycobacterium Bovis, Mycobacterium africanum, Mycobacterium microtii*, and *Mycobacterium leprae.*

9. The method of claim 1, wherein the microorganism is a fungus selected from among *Actinomyces, Aspergillus, Blatomyces, Candida, Cromoblastomices, Cocidios, Criptococcus, Dermatophitos, Fusarius, Histoplasma, Madura, Mocor, Nocardia, Paracocidius, Penicillinum, Phaeohyphomyces, Scedosporium*, and *Sporotricum.*

10. The method of claim 9, further comprising contacting the fungus with an agent selected from among Amphotericin, Caspofungin, Micafungin, Anidulafungin, Fluconazole, Flucytosine, Griseofulvin, Imidazole, Itraconazole, Ketoconazole, Miconazole, Nystatin, Posaconazole, Terbinafine, and Voriconazole.

11. The method of claim 1, wherein contacting the microorganism with the AQCs comprises administering the AQCs to a subject afflicted with a disease caused by the microorganism.

12. The method of claim 11, wherein the subject is afflicted with a disease-caused by antibiotic-resistant bacteria or nosocomial infections.

13. The method of claim 1, wherein contacting the microorganism with the AQCs comprises (a) adding the AQCs to a product, wherein the product is selected from among a phytosanitary product, a cosmetic product, a disinfectant product, an in vitro clinical diagnostic test kit, a paint, a sealant, a polymer, and a plastic; and (b) contacting the product obtained in (a) which comprises the AQCs with the microorganism.

14. The method of claim 13, wherein the products comprising the AQCs are used in: water treatment, construction, automotive, textile, hospital, or surgical materials.

* * * * *